(12) United States Patent
Kadobayashi et al.

(10) Patent No.: US 9,220,663 B2
(45) Date of Patent: Dec. 29, 2015

(54) DENTAL COMPOSITION

(75) Inventors: Yusei Kadobayashi, Kyoto (JP); Masako Shigezawa, Kyoto (JP); Keiji Takahashi, Kyoto (JP)

(73) Assignee: KABUSHIKI KAISHA SHOFU, Kyoto (JP)

(*) Notice: Subject to any disclaimer, the term of this patent is extended or adjusted under 35 U.S.C. 154(b) by 664 days.

(21) Appl. No.: 13/218,779

(22) Filed: Aug. 26, 2011

(65) Prior Publication Data
US 2013/0030080 A1 Jan. 31, 2013

(30) Foreign Application Priority Data
Jul. 29, 2011 (JP) ................................. 2011-166308

(51) Int. Cl.
*A61K 6/00* (2006.01)
*A61K 6/06* (2006.01)
*A61K 6/083* (2006.01)

(52) U.S. Cl.
CPC .................. *A61K 6/06* (2013.01); *A61K 6/0005* (2013.01); *A61K 6/0008* (2013.01); *A61K 6/0058* (2013.01); *A61K 6/0094* (2013.01); *A61K 6/083* (2013.01)

(58) Field of Classification Search
None
See application file for complete search history.

(56) References Cited

U.S. PATENT DOCUMENTS

| | | | |
|---|---|---|---|
| 4,459,193 A | 7/1984 | Ratcliffe et al. | |
| 4,674,980 A * | 6/1987 | Ibsen et al. | 433/228.1 |
| 4,962,151 A | 10/1990 | Mellon | |
| 5,116,885 A | 5/1992 | Hattori et al. | |
| 2002/0128347 A1 | 9/2002 | Blackwell et al. | |
| 2008/0319380 A1* | 12/2008 | Prabhu et al. | 604/60 |
| 2010/0226820 A1 | 9/2010 | Prabhu et al. | |

FOREIGN PATENT DOCUMENTS

| | | |
|---|---|---|
| EP | 0 273 657 | 7/1988 |
| GB | 1 544 776 | 4/1979 |

OTHER PUBLICATIONS

McGeary, Mechanical Packing of Spherical Particles, Journal of the American Ceramic Society, vol. 44, No. 10, pp. 514-522, 1961.*
U.S. Office Action issued Dec. 21, 2012 in U.S. Appl. No. 13/408,050.
Office Action issued Apr. 3, 2015 in corresponding U.S. Appl. No. 13/408,050.
Extended European Search Report issued Jan. 9, 2015 in corresponding European Application No. 12178522.4.
Final Office Action issued Sep. 8, 2015 in co-pending related U.S. Appl. No. 13/408,050.
Final Office Action issued Nov. 6, 2014 in corresponding U.S. Appl. No. 13/408,050.

* cited by examiner

*Primary Examiner* — Nicole M Buie-Hatcher
*Assistant Examiner* — Chelsea M Christensen
(74) *Attorney, Agent, or Firm* — Wenderoth, Lind & Ponack, L.L.P.

(57) ABSTRACT

There is provided a dental composition comprising at least one kind of filler and resin matrix, wherein the at least one kind of filler comprises a population of particles, wherein the population of particles has an average particle size from 110 to 500 μm, the maximum particle size of the population of particles is less than 1.4 times the average particle size, and the D30 of particle size distribution of the population of particles is no less than 0.9 times the average particle size.

20 Claims, 2 Drawing Sheets

DENTAL COMPOSITION

FIELD OF THE INVENTION

The present invention relates to a composition used in dental field. The present invention also relates to a dental prosthesis such as artificial teeth.

BACKGROUND ART

Dental compositions comprising filler and resin matrix are widely used as dental materials for the restoration of portion missing from a tooth or for the production of dental prostheses including artificial teeth. For cured dental compositions, patients require good mechanical strength, hardness and adequate color tone comparable with their natural teeth as well as abrasion resistance in the oral cavity during mastication. In addition, dentists and dental technicians require dental compositions when they are in the form of paste, i.e. dental compositions before they are cured, to keep them being stable, easy to shape and easy to fill in a metal mold so that they can treat the paste easily. Dental technicians also desire cured dental compositions that can give grinding and polishing feelings similar to those of natural teeth.

Dental compositions are set from paste to give cured product in and outside the oral cavity. For example, a dental composition in the form of paste may be filled in an odontic defect and cured there in the oral cavity. Outside the oral cavity, a dental composition in the form of paste is shaped to a dental prosthesis and then cured. The important thing upon curing the paste into the cured product is volumetric shrinkage associated with the polymerization curing. Particularly, high inner stress and cracks may occur at the interface between the tooth and the dental composition or on the inside of the prostheses, resulting in low adhesion and poor mechanical strength of the filled materials or the prostheses.

Conventional dental materials had comprised quartz particles as filler of which particle size was relatively large, as large as about 150 μm. Dental materials containing such large size filler possessed practically acceptable mechanical strength. The degree of shrinkage of the material upon polymerization of the material in the form of paste was also practically acceptable. However, the cured materials could provide only unsatisfying grinding and polishing feelings to the dental technicians and insufficient abrasion resistance to the patients.

A dental material containing ultrafine silica particles as filler having a particle size from 0.01 to 0.05 μm was developed. The dental material was excellent in grinding feeling and can easily be processed to provide a smooth surface. However, the amount of the ultrafine particle filler in the dental material is limited due to high viscosity of the material containing a high amount of the filler when it is in the form of paste. Therefore, a cured product obtained from the paste of the dental material had unfavorable mechanical strength and abrasion resistance. In addition, degree of shrinkage of the material upon polymerization was also unfavorable. A hybrid-type dental material which had advantages of both aforementioned dental materials had been developed (JP-A 63-88110).

Various polymerizable monomers and polymerization initiators for resin matrix of dental materials also have been proposed to give improved dental materials that satisfy the aforementioned needs of dental technicians and patients. In addition to the improvement of resin matrix, polymerizable agents were also proposed and new dental materials were developed. Fillers of submicron average particle size were also developed and used for dental materials.

RELATED PRIOR ART

[Patent Literature 1] JP-A 63-88110

SUMMARY OF THE INVENTION

Problem to be Solved by the Invention

Conventional dental materials had been developed on the premise that dental technicians grind the cured product of a dental material by hand with a dental router. Under the situation, the particle sizes of filler in dental materials have decreased from about 150 μm to submicron. However, the dental compositions containing submicron filler particles had a poor abrasion resistance that did not meet the needs of patients.

The present inventors have intensively studied so as to achieve a dental composition that can provide tough and hard cured product. Then, the inventors had found that a dental material containing filler particles of large average particle size can provide a cured product being easily processed by a mechanical grinding apparatus to give a ground product excellent in mechanical strength and abrasion resistance.

In one embodiment, the present invention provides a dental composition comprising at least one kind of filler and resin matrix, wherein the at least one kind of filler comprises a first population of particles, wherein the first population of particles has an average particle size from 110 to 500 μm, the maximum particle size of the first population of particles is less than 1.4 times the average particle size, and the D30 of particle size distribution of the first population of particles is no less than 0.9 times the average particle size.

In a preferred embodiment, the first population of particles in the dental composition may be any of inorganic particles, organic particles and organic-inorganic composite particles.

In other embodiment, the present invention provides a dental composition comprising at least one kind of filler and resin matrix, wherein the at least one kind of filler comprises a first population of particles, wherein the first population of particles has an average particle size from 110 to 500 μm, preferably from 200 to 500 μm, further preferably from 300 to 500 μm, and still further preferably from 400 to 500 μm, the maximum particle size of the first population of particles is less than 1.4 times the average particle size, and the D30 of particle size distribution of the first population of particles is no less than 0.9 times the average particle size.

In a preferred embodiment, the present invention further provides a dental composition comprising at least one kind of filler and resin matrix, wherein the at least one kind of filler comprises a first population of particles and a second population of particles, wherein the first population of particles has an average particle size from 110 to 500 μm, preferably from 200 to 500 μm, further preferably from 300 to 500 μm, and still further preferably from 400 to 500 μm, the maximum particle size of the first population of particles is less than 1.4 times the average particle size thereof, the D30 of particle size distribution of the first population of particles is no less than 0.9 times the average particle size thereof, the average particle size ratio of the second population of particles to the first population of particles (=[average particle size of the second population of particles]/[average particle size of the first population of particles]) is from 0.1 to 0.3 and preferably from 0.15 to 0.25, and the weight amount ratio of the second population of particles to the first population of particles (=[weight amount of the second population of particle]/[weight amount of the first population of particles]) is from 0.05 to 0.5 and preferably from 0.05 to 0.3.

In a preferred embodiment, the first population of particles in the dental composition may be made from any of inorganic material, organic material and organic-inorganic composite material, and the second population of particles in the dental composition may be made from any of inorganic material, organic material and organic-inorganic composite material.

Further, the present invention provides a dental composition comprising at least one kind of filler and resin matrix, wherein the at least one kind of filler comprises the first population of inorganic particles and the second population of inorganic particles, wherein the first population of inorganic particles has an average particle size from 110 to 500 μm, preferably from 200 to 500 μm, further preferably from 300 to 500 μm, and still further preferably from 400 to 500 μm, the maximum particle size of the first population of particles is less than 1.4 times the average particle size thereof, the D30 of particle size distribution of the first population of particles is no less than 0.9 times the average particle size thereof, the average particle size ratio of the first population of particles to the second population of particles is from 0.1 to 0.3 and preferably from 0.15 to 0.25, and the weight amount ratio of the first population of particles to the second population of particles is from 0.05 to 0.5 and preferably from 0.05 to 0.3.

In one embodiment, a cured product can be mechanically ground with an automatic program-controlled grinding machine to give dental prosthesis with an excellent abrasion resistance, mechanical strength and surface smoothness. In other embodiment, there is provided a dental composition for producing cured products. In one embodiment, a dental composition in the form of the paste, being excellent in stability and space-filling property to a metal mold, is provided.

BRIEF DESCRIPTION OF THE DRAWING

FIG. 1b shows a relative frequency curve and a relative cumulative frequency curve for a population of particles in a sample. The x-axis represents particle size of particles in a sample [μm]. The first vertical axis (on the left) represents relative frequency [%] of the population of particles in the sample. The second vertical axis (on the right) represents relative cumulative frequency [%] of the population of particles in the sample. The diamond (♦) indicates data of relative frequency of the population of particles in the sample. The open circle (○) indicates data of relative cumulative frequency of the population of particles in the sample. The dashed line represents a relative frequency curve (R) for the population of particles in the sample. The solid line represents a relative cumulative frequency curve (C) for the population of particles in the sample.

In the present application, the term "dental composition" means a composition which can be used in dental field. The dental composition of the present invention comprises at least one kind of filler and resin matrix.

In an embodiment, the at least one kind of filler in the dental composition of the present invention may be those made from inorganic material, organic material, or organic-inorganic composite material. In one embodiment, the at least one kind of filler in the dental composition may be inorganic filler, organic filler, or organic-inorganic composite filler. In a preferred embodiment, the at least one kind of filler in the dental composition is inorganic filler.

In one embodiment, the inorganic filler in the dental composition of the present invention may be those made from any inorganic material that can generally be used in dental compositions, without any limitation. Examples of inorganic materials include, but are not limited to, quartz, amorphous silica, aluminum silicate, aluminum oxide, titanium oxide, zirconium oxide, various glasses (including a glass made by a melting process and a synthesized glass made by a sol-gel process, etc), calcium carbonate, talc, kaolin, clay, mica, aluminum sulfate, calcium sulfate, barium sulfate, calcium phosphate, hydroxyapatite, silicon nitride, aluminum nitride, titanium nitride, silica carbide, boron carbide, calcium hydroxide, strontium hydroxide, and zeolite. Preferred are glasses such as aluminosilicate glass, borosilicate glass, aluminoborate glass, boroaluminosilicate glass containing sodium, fluorine, and/or heavy metal such as strontium, barium, or lanthanum. These inorganic materials can be used alone or in combination of two or more thereof.

In another embodiment, inorganic filler particles in the dental composition of the present invention may include cohesive inorganic filler that is obtained by cohering ultrafine inorganic particles such as Aerosil particles prepared by a gas-phase process and silica-zirconia oxide particles prepared by a sol-gel process in a solution. These inorganic filler particles can be used alone or in combination of two or more thereof.

In an embodiment, the inorganic filler in the dental composition of the present invention is glass particles. In a preferred embodiment, the filler is amino-silicate glass particles. In a more preferred embodiment, the chemical composition of the glass used in the present invention is from 60 to 90% by weight of $SiO_2$, from 5 to 20% by weight of $Al_2O_3$, and from 3 to 20% by weight of the other inorganic oxides based on the total glass composition. Examples of the other inorganic oxides include, but are not limited to, alkali metal oxide and coloring pigments. The glass used in the present invention may comprise at least one kind of alkali metal oxide selected from the group consisting of lithium oxide, beryllium oxide, sodium oxide, magnesium oxide, potassium oxide, calcium oxide, rubidium oxide, strontium oxide, cesium oxide, and barium oxide.

In an embodiment, the at least one kind of filler in the dental composition of the present invention may be those made from a known organic resin that is available as dental material. Examples of the organic resin include, but are not limited to, (meth)acrylate-based resin. In the present application, the term "(meth)acrylate" or "(meth)acryloyl" represents inclusively both acryloyl group-containing polymerizable monomers and methacryloyl group-containing polymerizable monomers.

In one embodiment, organic filler in the dental composition of the present invention may be those made from, but are not limited to, monofunctional monomers including (meth) acrylic acid esters such as methyl (meth)acrylate, ethyl (meth)acrylate, butyl (meth)acrylate, hexyl (meth)acrylate, tetrahydrofurfuryl (meth)acrylate, 2-hydroxyethyl(meth) acrylate, grycidyl (meth)acrylate, lauryl (meth)acrylate, cyclohexyl (meth)acrylate, benzil (meth)acrylate, allyl (meth)acrylate, 2-ethoxyethyl (meth)acrylate, methoxy polyethylene glycol (meth)acrylate, glycerol (meth)acrylate and isobonyl (meth)acrylate; silane compounds such as γ-(meth) acryloyloxypropyltrimethoxysilane and γ-(meth)acryloyloxypropyltriethoxysilane; nitrogen-containing compounds such as 2-(N,N-dimethylamino)ethyl (meth)acrylate, N-methylol (meth)acrylamide and diacetone (meth)acrylamide, aromatic bifunctional monomers such as 2,2-bis(4-(meth) acryloyloxyphenyl)propane, 2,2-bis(4-(3-(meth)acryloyloxy-2-hydroxypropoxy)phenyl)propane, 2,2-bis(4-(meth) acryloyloxyethoxyphenyl)propane, 2,2-bis(4-(meth) acryloyloxydiethoxyphenyl)propane, 2,2-bis(4-(meth) acryloyloxytetraethoxyphenyl)propane, 2,2-bis(4-(meth) acryloyloxypentathoxyphenyl)propane, 2,2-bis(4-(meth) acryloyloxydipropooxyphenyl)propane, 2,2-bis(4-(meth) acryloyloxyethoxyphenyl)-2-(4-(meth) acryloyloxydiethoxyphenylpropane, 2-(4-(meth) acryloyloxydiethoxyphenyl)-2-(4-(meth) acryloyloxytriethoxyphenyl)propane, 2-(4-(meth) acryloyloxydipropoxyphenyl)-2-(4-(meth) acryloyloxytriethoxyphenyl)propane, 2,2-bis(4-(meth) acryloyloxydipropoxyphenyl)propane and 2,2-bis(4-(meth) acryloyloxyisopropoxyphenyl)propane, aliphatic bifunctional monomers such as 2-hydroxy-3-acryloyloxypropylmethacrylate, hydroxypivalic acid neopentylglycol di(meth)acrylate, ethylene glycol di(meth)acrylate, diethylene glycol di(meth)acrylate, triethylene glycol di(meth)acrylate, butylene glycol di(meth)acrylate, polyethylene glycol di(meth)acrylate, neopentyl glycol di(meth) acrylate, propylene glycol di(meth)acrylate, 1,3-butanediol di(meth)acrylate, 1,4-butanediol di(meth)acrylate, 1,6-hexanediol di(meth)acrylate and glycerin di(meth)acrylate, trifunctional monomers such as trimethylolpropane tri (meth)acrylate, treimethylolethane tri(meth)acrylate, trimethylolmethane tri(meth)acrylate and pentaerythritol tri (meth)acrylate, tetrafunctional monomers such as pentaerythritol tetra (meth)acrylate and ditrimethylolporpane tetra(meth)acrylate.

In an embodiment, the filler in the dental composition of the present invention may be those made from a known organic-inorganic composite material that can be used as dental material. The organic-inorganic composite filler used in the present invention may be powders which are obtained by mixing inorganic filler particles and polymerizable monomers, polymerizing the mixture and pulverizing the polymerized mixture. In the organic-inorganic composite material, the inorganic filler particles are dispersed in the polymer matrix. In one embodiment, the inorganic filler particles in the organic-inorganic composite material may be any of the aforementioned materials that can be used in the dental composition of the present invention as inorganic filler. Examples of the inorganic fillers may be, without any limitation, colloidal silica (e.g., trade name: Aerosil R972, Aerosil 200, Aerosil 380, Aerosil 50 (Nippon Aerosil Co., Ltd.)). In another embodiment, the polymer matrix constituting the organic-inorganic composite filler in the dental composition of the present invention may be any of the aforementioned materials that are used in the dental composition of the present invention as inorganic filler.

In an aspect, the at least one kind of filler in the dental composition of the present invention comprises a first population of particles, wherein the first population of particles has an average particle size from 110 to 500 μm, the maximum particle size of the first population of particles is less than 1.4 times the average particle size, and the D30 of particle size distribution of the first population of particles is no less than 0.9 times the average particle size.

In a preferred aspect, the at least one kind of filler in the dental composition of the present invention further comprises a second population of particles in addition to the first population of particles, wherein the second population of particles preferably has, without any limitation, an average particle size from 20 to 112 μm, the maximum particle size of the second population of particles is less than 1.4 times the average particle size thereof, and the D30 of particle size distribution of the second population of particles is no less than 0.8 times the average particle size thereof.

In a more preferred aspect, the first population of particles and the second population of particles are inorganic particles, respectively.

In a preferred embodiment, the at least one kind of filler in the dental composition of the present invention comprises a first population of particles and a second population of particles, wherein the minimum particle size of the first population of particles is 80 μm and/or the minimum particle size of the second population of particles is 10 μm.

In a more preferred embodiment, the at least one kind of filler in the dental composition of the present invention comprises a first population of particles and a second population of particles, wherein the average particle size ratio of the first population of particles to the second population of particles is from 0.1 to 0.3 and preferably from 0.15 to 0.25, and the weight amount ratio of the first population of particles to the second population of particles is from 0.05 to 0.5 and preferably from 0.05 to 0.3.

In still further preferred embodiments, the first population of particles and the second population of particles are inorganic particles, respectively.

In an embodiment, the amount of the at least one kind of filler is from 65.0 to 99.5% by weight, preferably from 70 to 98% by weight, and more preferably from 80 to 95% by weight based on the total weight amount of the dental composition. In other embodiment, the dental composition comprises the at least one kind of filler from 65.0 to 99.5% by weight and the resin matrix from 0.5 to 35.0% by weight based on the total amount of the dental composition.

In other embodiment, the at least one kind of filler in the dental composition of the present invention comprises a first population of particles, a second population of particles and a third particle. In one embodiment, the third particle has an average particle size from 1 nm to 1 μm. In a preferred embodiment, the third particle may be, without any limitation, colloidal silica (e.g., trade name: Aerosil R972, Aerosil 200, Aerosil 380, Aerosil 50 (Nippon Aerosil Co., Ltd.)). The average particle size of the third particle is about 16 nm (Aerosil R972), 12 nm (Aerosil 200), 7 nm (Aerosil 380), and 30 nm (Aerosil 50), respectively.

In the present application, "particle size" is determined on the basis of number-size distribution and obtained by: imaging the particles with a microscope and measuring unidirectional particle diameters (Green diameters) of the particles on the image. In the present application, "average particle size"

is an arithmetic mean of particle sizes obtained from measuring plural particles as described above. An average particle size may be calculated, without any limitation, from particle sizes of a thousand particles in a sample measured as described above. A "maximum particle size" and a "minimum particle size" of the particles in a sample are a maximum size and a minimum size in the number-particle size distribution obtained from the plural particle sizes measured as described above, respectively. The maximum particle size and the minimum particle size are determined, without any limitation, from particle sizes of a thousand particles in the sample measured as described above.

Figure 1:
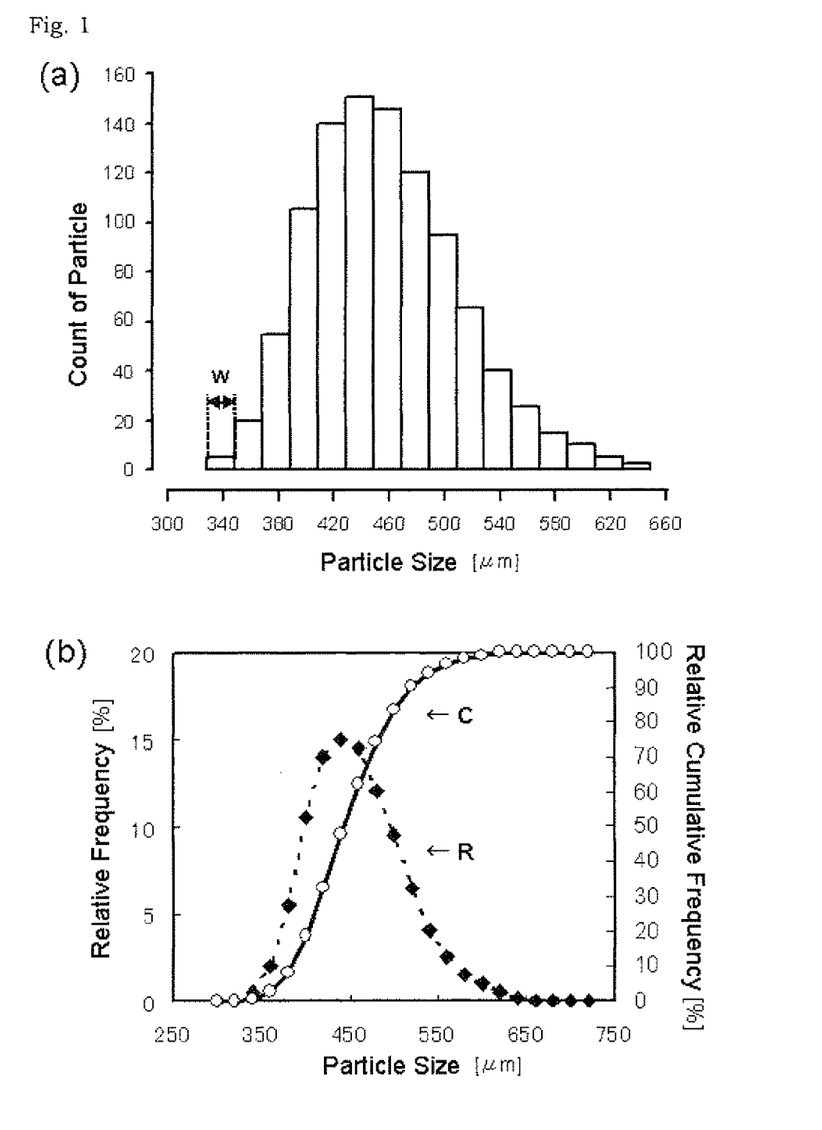
FIG. 1a shows a particle size histogram of a population of particles in a sample. The x-axis represents median value of particle size range as to each bin [μm]. The y-axis represents count of particles for each bin. The "w" represents a bin width.

The term "D30 of particle size distribution" used in the present application is a statistic particle size for a population of particles in a sample which is obtained as follows. Particles in a sample are measured to obtain the particle sizes and the total number (n) of particles which is used to calculate the number of bins with square-root choice ($\sqrt{n}$) or Sturges' formula ($[\log_2 n+1]$) without any limitation. The number of bins is an integer number, which may be any of the results of the calculations above, any integer number between the results, or a number obtained by rounding off any one of the results. A range of particle size is set on the basis of the particle size date of the population of particles, which is from the minimum to the maximum particle size. The range of particle size is divided by the number of bins to obtain a width of bin (w). The width of bin (w) is an integer number, which may be the result of the above calculation or a number obtained by rounding off the result. The bin width (w) is, but is not limited to, 30 μm, 20 μm, 15 μm, 10 μm, 5 μm or 1 μm. To obtain a frequency table, the particle size data within the range of particle size are split into bins (classes). Then for each bin, the number of split data falling into each bin is counted. The bins are plotted on the x-axis and their counts for each bin (frequencies) are plotted on the y-axis to construct a histogram (FIG. 1a). The values on the x-axis in FIG. 1a represent median value of particle size range as to each bin.

Based on the frequency table, relative frequencies (%) and cumulative relative frequencies (%) can be calculated. Calculated relative frequencies (FIG. 1a, diamond; ♦) and calculated cumulative relative frequencies (FIG. 1a, open circle; ○) are plotted on the same figure (FIG. 1b) to draw a relative frequency curve (FIG. 1b, dashed line; R) and a relative cumulative frequency curve (solid line; C), respectively. A "D30 of particle size distribution" is the x-coordinate when the cumulative relative frequency is 30% based on the cumulative relative frequency curve (C). The D30 of particle size distribution is determined on the basis of the particle size date obtained by measuring a thousand particles in a sample.

In an embodiment, the filler of the dental composition of the present invention may be commercially available raw particles that can be generally used as filler material. The raw particles can be pulverized to have a desired average particle size. The pulverizing procedure may be that commonly used in dental field, such as a wet process or a dry process, but is not limited to these processes. Examples are a high-speed rotation mill such as a hammer mill and a turbo mill, a container-driven medium mill such as a ball mill and an oscillating mill, a grinding medium agitating mill such as a sand grinder and an attritor, and a jet mill. The pulverizing procedure can be appropriately selected from them depending upon the desired average particle size. In order to obtain particles having a relatively-small average particle size, a wet-grinding in an aqueous medium is a preferred mode. As the aqueous medium used in the case, water may be used alone or in combination of alcohols, ethers, ketones and the like which are miscible with water. The conditions for the wet-grinding vary depending upon a size, a hardness or an amount of particles to be added, and a kind of and an amount of an aqueous medium to be added. The conditions including grinding condition may be appropriately selected depending upon the desired average particle size of particles.

In a preferred embodiment, the particles as filler in the dental composition of the present invention can be prepared by a chemical vapor deposition reaction, a sol-gel reaction, a suspension polymerization reaction, dispersion polymerization reaction or the like, without any limitation.

In an embodiment, the degree of circularity of particles in the dental composition of the present invention ranges from 0.7 to 1.0, preferably from 0.9 to 1.0, and more preferably from 0.95 to 1.00.

The degrees of circularity of particles were determined by taking an image of the particles with a light microscope or a scanning electron microscope (SEM) and analyzing the image with an image analyzer to obtain the boundary lengths (L) and area (S) of particles. The number of particles per the sample was 50 particles or more.

In an embodiment, the refractive index of at least one kind of filler in the dental composition of the present invention is from 1.46 to 1.58 and preferably from 1.49 to 1.54. In other embodiment, the difference in refractive index between the at least one kind of filler and the resin matrix of the dental composition of the present invention is 0.03 or less and preferably 0.01 or less.

The resin matrix of the dental composition of the present invention comprises a polymerizable monomer and a polymerization initiator. The above polymerizable monomer may be known monofunctional or multifunctional polymerizable monomers which are generally used as dental composition. In an embodiment, the polymerizable monomers are preferably those having an acryloyl group and/or a methacryloyl group.

Examples of polymerizable monomers having no acidic group may include, but are not limited to, monofunctional monomer, e.g., (meth)acrylic acid esters such as methyl (meth)acrylate, ethyl (meth)acrylate, butyl (meth)acrylate, hexyl (meth)acrylate, tetrahydrofurfuryl (meth)acrylate, 2-hydroxyethyl(meth)acrylate, grycidyl (meth)acrylate, lauryl (meth)acrylate, cyclohexyl (meth) acrylate, benzil (meth)acrylate, allyl (meth)acrylate, 2-ethoxyethyl (meth)acrylate, methoxy polyethylene glycol (meth)acrylate, glycerol (meth)acrylate and isobonyl (meth) acrylate; silane compounds such as γ-(meth)acryloyloxypropyltrimethoxysilane and γ-meth)acryloyloxypropyltriethoxysilane; nitrogen-containing compounds such as 2-(N,N-dimethylamino)ethyl (meth)acrylate, N-methylol (meth) acrylamide and diacetone (meth)acrylamide, aromatic bifunctional monomer, e.g., 2,2-bis(4-(meth) acryloyloxyphenyl)propane, 2,2-bis(4-(3-(meth)acryloyloxy-2-hydroxypropoxy)phenyl)propane, 2,2-bis(4-(meth) acryloyloxyethoxyphenyl)propane, 2,2-bis(4-(meth) acryloyloxydiethoxyphenyl)propane, 2,2-bis(4-(meth) acryloyloxytetraethoxyphenyl)propane, 2,2-bis(4-(meth) acryloyloxypentaethoxyphenyl)propane, 2,2-bis(4-(meth) acryloyloxydipropoxyphenyl)propane, 2(4-(meth) acryloyloxyethoxyphenyl)-2-(4-(meth) acryloyloxydiethoxyphenyl)propane, 2-(4-(meth) acryloyloxydiethoxyphenyl)-2-(4-(meth) acryloyloxytriethoxyphenyl)propane, 2-(4-(meth) acryloyloxydipropoxyphenyl)-2-(4-(meth) acryloyloxytriethoxyphenyl)propane, 2,2-bis(4-(meth) acryloyloxydipropoxyphenyl)propane and 2,2-bis(4-(meth) acryloylosopropoxyphenyl)propane, aliphatic bifunctional monomer, e.g., 2-hydroxy-3-acryloyloxypropylmethacrylate, hydroxypivalic acid neopentylglycol di(meth)acrylate, ethylene glycol di(meth)acrylate, diethylene glycol di(meth)acrylate, triethylene glycol di(meth)acrylate, butylene glycol di(meth)acrylate, polyethylene glycol di(meth)acrylate, neopentyl glycol di(meth) acrylate, propylene glycol di(meth)acrylate, 1,3-butanediol di(meth)acrylate, 1,4-butanediol (meth)acrylate, 1,6-hexanediol di(meth)acrylate, and glycerin di(meth)acrylate, trifunctional monomer, e.g., trimethylolpropane tri(meth)acrylate, treimethylolethane tri(meth)acrylate, trimethylolmethane tri(meth)acrylate and pentaerythritol tri(meth)acrylate, tetrafunctional monomer, e.g., pentaerythritol tetra(meth)acrylate and ditrimethylolporpane tetra(meth)acrylate.

Examples of urethane-based polymerizable monomers may include, but are not limited to, di(meth)acrylates having a bifunctional or trifunctional or more-functional urethane linkage which are derived from an adduct of a polymerizable monomer having a hydroxy group such as 2-hydroxyethyl (meth)acrylate, 2-hydroxypropyl (meth)acrylate and 3-chloro-2-hydroxypropyl (meth)acrylate, and a diisocyanate compound such methylcyclohexane diisocyanate, methylene bis(4-cyclohexyl isocyanate), isophorone diisocyanate, diisocyanate methylbenzene and 4,4-diphenylmethane diisocyanate.

In addition to the aforementioned (meth)acrylate-based polymerizable monomers, other polymerizable monomers, for example, a monomer, an oligomer or a polymer having at least one polymerizable group in the molecule may be used for resin matrix of the dental composition of the present invention, depending upon any purpose. In an embodiment, the polymerizable monomers may have a substituent such as an acidic group and a fluoro group in the same molecule. In the present invention, a polymerizable monomer may be a single component and a mixture of a plurality of polymerizable monomers. In addition, when a polymerizable monomer possesses the extremely high viscosity at room temperature or when a polymerizable monomer is a solid at room temperature, it is preferably used in a mixture of said polymerizable monomers with a polymerizable monomer having the low viscosity. The mixture may comprise two kinds, three kinds or more of polymerizable monomers.

In an embodiment, resin matrix of the dental composition of the present invention may include only monofunctional polymerizable monomers, and may additionally include polyfunctional polymerizable monomers. In a preferred embodiment, resin matrix of the dental composition of the present invention may include an aromatic compound of a bifunctional polymerizable monomer and an aliphatic compound of a bifunctional polymerizable monomer. In a more preferred embodiment, resin matrix of the dental composition of the present invention includes 2,2-bis(4-(3-methacryloyloxy-2-hydroxypropoxy)phenyl)propane (Bis-GMA) and triethylene glycol dimethacrylate (TEGDMA).

In an embodiment, resin matrix of the dental composition of the present invention may include polymerizable monomers containing an acid group such as a phosphoric acid group, a carboxylic acid group, a sulfonic acid group or the like in the molecule as a part or the whole of the polymerizable monomer so as to impart a property adhering to the teeth substance and a nonprecious metal to the dental composition of the present invention. In another embodiment, in order to enhance a precious metal adhering property, resin matrix of the present invention may include polymerizable monomers containing a sulfur atom in the molecule. In this context of enhanced adhering property, the embodiments of resin matrix may include, but are not limited to, carboxylilc acid group-containing polymerizable monomers, e.g., (meth)acrylic acid, 1,4-di(meth)acryloyloxyethyl-pyromellitic acid, 6-(meth)acryloyloxynaphtalene-1,2,6-tricarboxylic acid, N-(meth)acryroyl-p-aminobenzoic acid, N-(meth)acryroyl-5-aminosalicylic acid, 4-(meth)acryroyloxyethyltrimellic acid and anhydride thereof, 4-(meth)acryroyloxybutyltrimellic acid and anhydride thereof, 2-(meth)acryroyloxybenzoic acid, β-(meth)acryroyloxyethyl hydrogen succinate, β-(meth)acryroyloxyethyl hydrogen maleate, 11-(meth)acryloyloxy-1,1-undecanedicarboxylic acid and p-vinylbenzoic acid; phosphate group-containing monomers, e.g., 2-(meth)acryloyloxyethyl hydrogen phosphate, 3-(meth)acryloyloxypropyl dihydrogen phosphate, 10-(meth)acryloyloxydecyl hydrogen phosphate, bis(2-(meth)acryloyloxyethyl) dihydrogen phosphate and 2-(meth)acryloyloxyphenyl hydrogen phosphate; sulfonic group-containing monomers, e.g., 2-(meth)acrylamide-2-methylpropanesulfonic acid, 4-(meth)acryloyloxybenzenesulfonic acid and 3-(meth)acryloyloxypropanesulfonic acid; sulfur atom-containing monomers, e.g., (meth)acrylate having a triazinethiol group, (meth)acrylate having a mercapto group, (meth)acrylate having a polysulfide group, (meth)acrylate having a thiophosphate group, (meth)acrylate having a disulfide cyclic group, (meth)acrylate having a mercaptodithiazole group, (meth)acrylate having a thiouracil group and (meth)acrylate having a thiirane group.

These polymerizable monomers may be used alone or in mixture of two or more kinds.

In the present invention, a polymerization initiator may include, but is not limited to, a known radical generator. Polymerization initiators are generally classified into chemical polymerization initiator that initiates polymerization by mixing prior to use, thermal polymerization initiator that initiates polymerization by heating or warming, and photoinitiator that initiates polymerization by light irradiation.

In an embodiment, a chemical polymerization initiator may include, but is not limited to, polymerization initiator systems of a redox type comprising an organic peroxide/an amine compound or an organic peroxide/an amine compound/a sulfinic acid salt, or an organic peroxide/an amine compound/a borate compound, and organometal type initiator systems which initiate polymerization by a reaction with oxygen or water. In a chemical polymerizable initiator, sulfinic acid salts and borate compounds can also initiate the polymerization by a reaction with a polymerizable monomer having an acidic group.

Examples of the aforementioned organic peroxides include, but are not limited to, benzoylperoxide, parachlorobenzoylperoxide, 2,4-dichlorobenzoyl peroxide, acetyl peroxide, lauroyl peroxide, tertiary-butyl peroxide, cumene hydroperoxide, 2,5-dihydroperoxy-2,5-dimethylhexane, methyl ethyl ketone peroxide, and tertiary-butyl peroxide benzoate. Examples of the aforementioned amine compounds include, but are not limited to, a secondary or tertiary amine in which an amine group is bound to an aryl group, and particular examples thereof are p-N,N-dimethyltoluidine, N,N-dimethylaniline, N-β-hydroxyethylaniline, N,N-di(β-hydroxyethyl)aniline, p-N,N-di(β-hydroxyethyl)toruidine, N-methylaniline, and p-N-methyltoluidine. Examples of the aforementioned sulfinic acid salts include, but are not limited to, sodium benzenesulfinate, lithium benzenesulfinate, and sodium p-toluenesulfinate. Examples of the aforementioned borate compounds include, but are not limited to, trialkylphenylboron, and a sodium salt, a lithium salt, a potassium salt, a magnesium salt, a tetrabutyl ammonium salt and a tetramethyl ammonium salt of trialkyl (p-fluorophenyl)boron (wherein the alkyl group is n-butyl group, n-octyl group, n-dodecyl group or the like). Examples of the aforementioned organometal type polymerizable initiators include, but are not limited to, organic boron compounds such as triphenylborane, tributylborane, and a partial oxide of tributylborane.

In an embodiment, azo compounds such as azobisisobutyronitrile, methyl azobisisobutyrate and azobiscyano valeric acid may be used as a thermal polymerization initiator by heating or warming in addition to the aforementioned organic peroxide.

In another embodiment, photoinitiators may be a photosensitizer. The photosensitizer may be used alone as a photoinitiator or in combination with a photopolymerization promotor. Examples of the aforementioned photosensitizers include, but are not limited to, α-diketones such as benzil, camphorquinone, α-naphtil, acetonaphtone, p,p'-dimethoxybenzil, p,p'-dichlorobenzylacetyl, pentadione, 1,2-phenanthrenquinone, 1,4-phenanthrenquinone, 3,4-phenanthrenquinone, 9,10-phenanthrenquinone and naphthoquinone; benzoin alkyl ethers such as benzoin, benzoin methyl ether and benzoin ethyl ether; thioxanthones such as thioxanthone, 2-chlorothioxanthone, 2-methylthioxanthone, 2-isopropylthioxanthone, 2-methoxythioxanthone, 2-hydroxythioxanthone, 2,4-diethylthioxanthone and 2,4-diisopropylthioxanthone; benzophenones such as benzophenone, p-chlorobenzophenone and p-methoxybenzophenone; acylphosphineoxides such as 2,4,6-trimethylbenzoyl diphenylphosphineoxide and bis(2,6-dimethoxybenzoyl)-2,4,4-trimethylpentylphosphineoxide; α-aminoacetophenones such as 2-benzyl-dimethylamino-1-(4-morpholinophenyl) butanone-1,2-benzyl-diethylamino-1-(4-morpholinophenyl) propanone-1; ketals such as benzyldimethylketal, benzyldiethylketal and benzyl(2-methoxyethylketal); titanocenes such as bis(cyclopentadienyl)-bis[2,6-difluoro-3-(1-pyrolyl) phenyl]titanium, bis(cyclopentadienyl)-bis(pentanefluorophenyl)titanium and bis(cyclopentadienyl)-bis(2,3,5,6-tetrafluoro-4-disiloxyphenyl)-titanium.

Examples of the aforementioned photopolymerization promotors include, but are not limited to, tertiary amines such as N,N-dimethylaniline, N,N-di-n-butylaniline, N,N-dibenzylaniline, p-N,N-dimethyl-toluidine, m-N,N-dimethyltoluidine, p-N,N-diethyltoluidine, p-bromo-N,N-dimethylaniline, m-chloro-N,N-dimethylaniline, p-dimethylaminobenzaldehyde, p-dimethylaminoacetophenone, p-dimethylaminobenzoic acid, p-dimethylaminobenzoicacid ethyl ester, p-demtethylaminobenzoic acid amino ester, N,N-dimethylanthranilic acid methyl ester, N,N-dihydroxyethylaniline, p-N,N-dihydroxyethyl-toluidine, p-dimethylaminophenylalcohol, p-dimethylaminostyrene, N,N-dimethyl-3,5-xylidine, 4-dimethylaminopyridine, N,N-dimethyl-α-naphthylamie, N,N-dimethyl-β-naphthylamine, tributylamine, tripropylamine, triethylamine, N-methyldiethanolamine, N-ethyldiethanolamine, N,N-dimethylhexylamine, N,N-dimethyldodecylamine, N,N-dimethylstearylamine, N,N-dimethylaminoethyl methacrylate, N,N-diethylaminoethyl methacrylate and 2,2'-(n-butylimino) diethanol; secondary amines such as N-phenylglycine; barbituric acids such as 5-butylbarbituric acid and 1-benzyl-5-phenylbarbituric acid; tin compounds such as dibutyltin diacetate, dibutyltin dilaurate, dioctyltin dilaurate, dioctyltin diperacetate, dioctyltin bis(mercaptoacetic acid isooctyl ester) salt and tetramethyl-1,3-diacetoxydistannoxane; aldehyde compounds such as laurylaldehyde and terephthalaldehyde; sulfur-containing compounds such as dodecylmercaptan, 2-mercaptobenzooxazole, 1-decanethiol and thiosalicylic acid.

In another embodiment, resin matrix of the dental composition of the present invention may include, in addition to the aforementioned photopolymerization promotors, oxycarboxylic acids such as citric acid, maleic acid, tartaric acid, glycolic acid, gluconic acid, α-oxyisobutyric acid, 2-hydroxypropioic acid, 3-hydroxybutanoic acid 4-hydroxybutanoic acid, and dimethylolpropioic acid for improving the photopolymerization promoting ability.

In the present invention, those polymerization initiators may be used alone or in mixture of two or more thereof. In addition, these polymerization initiators can be used in combination thereof irrespective of the polymerization form and the kind of polymerization initiators. An amount of a polymerization initiator to be added may be appropriately selected depending upon the use. In general, the amount may be selected from a range of 0.1-10 parts by weight based on a polymerizable monomer.

In an embodiment, the polymerization initiator is a photopolymerization initiator. The dental composition which comprises a photopolymerization initiator is relatively easy to be polymerized without air bubble entrainment. In a preferred embodiment, the photopolymerization initiators is a combination of α-diketone and tertiary amine and is more preferably a combination of camphorquinone with an aromatic amine having an amino group directly bound to a benzene ring such as ethyl p-N,N-dimethylaminobenzoate or with an aliphatic amine having a double bond in the molecule such as N,N-dimethylaminoethyl methacrylate. In another embodiment, the dental composition of the present invention can comprise, depending upon the use, sensitizing pigments such as coumalin, cyanine, and thiazine; a light acid generator which produces Broensted acid or Lewis acid by light irradiator such as a s-triazine derivative substituted with a halomethyl group or diphenyl iodonium salt compound; quaternary ammonium halides; and transition metal compound.

In an embodiment, a resin of the dental composition of the present invention may be dyed with coloring pigments. The coloring pigments are classified into inorganic pigments and organic pigments. Examples of the inorganic pigments include, but are not limited to, chromates such as chrome yellow, zinc yellow and barium yellow; ferrocyanides such as Prussian blue; sulfides such as vermilion, cadmium yellow, zinc sulfide, antimony white and cadmium red; sulfates such as barium sulfate, zinc sulfate and strontium sulfate; oxides such as zinc white, titanium white, blood red, black iron oxide and chromium oxide; hydroxides such as aluminum hydroxide; silicates such as calcium silicate and ultramarine; and carbons such as carbon block and graphite. Examples of the organic pigments include, but are not limited to, nitoroso pigments such as Naphthol Green B and Naphthol Green Y; nitoro pigments such as Naphthol S and Lithol Fast Yellow 2G; insoluble azo pigments such as Permanent Red 4R, Brilliant Fast Scarlet, Hanza Yellow and Benzidine Yellow; poorly-soluble azo pigments such as Lithol Red, Lake Red C and Lake Red D; soluble azo pigments such as Brilliant Caramine 6B, Permanent Red F5R, Pigment Scarlet 3B and Bordeaux 10B; phthalocyanine pigments such as Phthalocyanine Blue, Phthalocyanine Green and Sky Blue; basic dye pigments such as Rhodamine Lake, Malachite Green Lake and Methyl Violet Lake; and acidic dye pigments such as Peacock Blue Lake, Eosin Lake and Quinoline Yellow Lake. These pigments may be used alone or in combination of two or more thereof. In an embodiment, the coloring pigment is an inorganic pigment, preferably titanium white, blood red, black iron oxide or yellow iron oxide.

The fillers used in the dental composition of the present invention may be inorganic particles of which surface is covered with poly(organo)siloxane. In an embodiment, the at least one kind of filler in the dental composition of the present invention may be silane-treated inorganic particles. In a preferred embodiment, the at least one kind of filler in the dental composition of the present invention is a dyed glass which are dyed by mixing silane-treated glass with a coloring pigment described above.

Glass can be dyed by mixing raw material glass with a coloring agent, without any limitation. Such coloring agents include, but are limited to, iron, manganese, copper, chromium, zirconium, cobalt, tin, titanium, nickel, and vanadium. Particular examples of the coloring agents is an iron oxide, a red oxide, a manganese dioxide, a manganese carbonate, a copper oxide, a chromium oxide, a zirconium silicate, a cobalt oxide G, a tin oxide, a titanium oxide, an iron silicate, a nickel oxide, an ammonium metavanadate, and a boron oxide.

The degree of coloring of glass is preferably adjusted according to the following range of Lab. The at least one kind of filler in the dental composition of the present invention is adjusted preferably for the following coloring by increasing and decreasing an amount of pigments.

$L^*=50$ to $75, a^*=-4$ to $-1, b^*=-8$ to $4$.

The dental composition of the present invention may comprise ultraviolet absorbing agents such as 2-hydroxy-4-methylbenzophenone; polymerization inhibitors such as a hydroquinone, a hydroquinone monomethyl ether and 2,5-di(tertiary-butyl)-4-methylphenol; anti-discoloring agents; antimicrobial agents; and other conventional known additives. A packing type of the dental composition of the present invention may be any of one-package type, two-package type and the like depending upon the kind of polymerization initiator or the purpose of use, and the packing type is appropriately selected depending upon the application.

The at least one kind of filler of the dental composition of the present invention is exposed to abrasion during mastication of foods. In an embodiment, Vickers hardness of the filler in the cured product of the dental composition is measured. The Vickers hardness of the filler is measured at six positions on a polished surface of test sample which has a diameter of 20 mm and a thickness of 3 mm, according to ISO 14705 (2000). The average of the measurement results at the six positions is used as Vickers hardness of the test sample. In an embodiment, the Vickers hardness (HV200) is in a range from 450 to 600. In a preferred embodiment, the Vickers hardness of the first population of particles is the same as that of the second population of particles. In a more preferred embodiment, the at least one kind of filler and the resin matrix used in the dental composition of the present invention have the same Vickers hardness except other components such as coloring pigment etc.

The dental composition of the present invention can be used, without any limitation, as materials for the production of a dental block or a dental prosthesis such as artificial tooth. Therefore, the present invention also provides a dental block or a dental prosthesis such as an artificial tooth as cured materials of the dental composition according to the present invention. In addition, in an embodiment the dental composition of the present invention can be used as a repairing agent for a dental prosthesis such as an artificial tooth.

In a preferred embodiment, a dental block prepared from the dental composition of the present invention is processed by a mechanical grinding apparatus that is controlled by a program in an automatic manner. Therefore, the present invention provides a dental block prepared from the dental composition of the present invention that can be processed by a CAD/CAM system. A CAD/CAM system comprises, without any limitation, a step of obtaining data on geometry in the oral cavity of a patient, designing a dental prosthesis such as an artificial tooth on a computer, and processing a dental block by an automatic mechanical grinding apparatus to give the dental prosthesis.

Cured products such as a dental block for processing with a CAD/CAM system are larger in size than those for conventional dental prosthesis such as artificial teeth. Internal stress on the inside the cured products caused by polymerization shrinkage of a dental composition in the form of the paste tends to increase with increasing size of the cured products. The increased internal stress causes the cured products to possess reduced physical properties such as mechanical strength.

In the present application, the term "dental prosthesis" includes, but is not limited to, an inlay, a clown, a bridge, and an artificial tooth.

In an embodiment, the dental composition of the present invention is used, without any limitation, for an enamel portion of artificial teeth. In other embodiment, the dental composition of the present invention can be dyed with coloring pigments depending upon a portion to be applied such as an enamel portion, a dentin portion and a cementum of artificial teeth.

EXAMPLES

Fine powders of glass shown in Table 1 were prepared by a melting and pulverizing process.

TABLE 1

| Component | Glass 1 (% by weight) | Glass 2 (% by weight) | Glass 3 (% by weight) | Glass 4 (% by weight) |
| --- | --- | --- | --- | --- |
| $SiO_2$ | 67 | 70 | 69 | 72 |
| $Al_2O_3$ | 13 | 13 | 10 | 10 |
| $B_2O_3$ | 18 | 15 | 18 | 15 |
| $Na_2O$ | 2 | 2 | 3 | 3 |
| Refractive index | 1.5195 | 1.5304 | 1.5204 | 1.5359 |
| Vickers hardness (HV200) | 520 | 535 | 530 | 538 |

The prepared fine glass powders, being dried, were dispersed in atmosphere at a high temperature to form spherical shaped glass particles. Glass 1 particles shown in Table 1 of which the degree of circularity is 0.95 or more were used in the examples. The average particle size, the maximum particle size, the minimum particle size, and the D30 of particle size distribution of the population of the fine glass powders used are shown in Table 2.

TABLE 2

| Fine glass powder | Average particle size | Maximum particle size | Minimum particle size | D30 of particle size distribution |
| --- | --- | --- | --- | --- |
| A | 482 | 630 | 350 | 443 |
| B | 390 | 503 | 285 | 368 |
| C | 168 | 224 | 124 | 154 |
| D | 115 | 153 | 82.4 | 107 |
| E | 312 | 423 | 240 | 293 |
| F | 640 | 854 | 453 | 589 |
| a | 111 | 140 | 63.0 | 89.3 |
| b | 76.5 | 113 | 42.5 | 68.6 |
| c | 25.3 | 34.2 | 13.5 | 21.5 |
| d | 18.4 | 25.6 | 9.8 | 15.1 |
| e | 159 | 234 | 83.5 | 122 |
| f | 10.1 | 15.3 | 3.1 | 8.1 |

The resin matrix was prepared by mixing 60 parts by weight of 2,2-bis(4-(3-methacryloyloxy-2-hydroxypropoxy)phenyl)propane (Bis-GMA), 40 parts by weight of triethylene glycol dimethacrylate (TEGDMA), 1 part by weight of dl-camphorquinone (CQ) and 1 part by weight of ethyl p-N,N-dimethylaminobenzoate (DMABE). The refractive index of the resin matrix was 1.5182.

Pastes were obtained by kneading the glass filler of Table 2 and the above resin matrix according to a formulating proportion shown in Table 3.

TABLE 3

| Sample | The first population of particles | The second population of particles | Average particle size ratio$^\alpha$ | Weight ratio$^\beta$ | Weight ratio of filler$^\gamma$ |
|---|---|---|---|---|---|
| Example 1 | A | — | — | — | 85% by weight |
| Example 2 | A | a | 0.23 | 0.28 | 85% by weight |
| Example 3 | B | b | 0.20 | 0.2 | 85% by weight |
| Example 4 | C | c | 0.15 | 0.25 | 85% by weight |
| Example 5 | D | d | 0.16 | 0.18 | 85% by weight |
| Example 6 | A | a | 0.23 | 0.35 | 85% by weight |
| Example 7 | A | a | 0.23 | 0.48 | 85% by weight |
| Example 8 | A | a | 0.23 | 0.12 | 85% by weight |
| Example 9 | A | a | 0.23 | 0.07 | 85% by weight |
| Example 10 | E | b | 0.25 | 0.23 | 85% by weight |
| Comparative example 1 | F | a | 0.17 | 0.28 | 85% by weight |
| Comparative example 2 | A | e | 0.33 | 0.25 | 85% by weight |
| Comparative example 3 | E | a | 0.36 | 0.28 | 85% by weight |
| Comparative example 4 | — | a | — | — | 85% by weight |
| Comparative example 5 | — | f | — | — | 85% by weight |

$^\alpha$Ratio of the average particle size of the second population of particles to the average particle size of the first population of particles (= [average particle size of the second population of particles]/[average particle size of the first population of particles]).
$^\beta$Weight ratio of the second population of particles to the first population of particles (= [weight of the second population of particles]/[weight of the first population of particles]).
$^\gamma$Weight ratio of the at least one kind of filler to the dental composition.

Stability of Paste

The dental compositions shown in Table 3 in the form of paste were shaped into a square pole with 5 mm×5 mm×50 mm, and the pastes shaped square pole were bent from 180 degree angle to 120 degree angle. The dental compositions were evaluated for the stability on the tensile side of the bent square pole according to the following evaluation criteria:

A: good stability, neither white turbidness nor shear cracking were found;

B: sufficient stability, white turbidness was found but shear cracking was hardly found;

C: unpractical stability, both white turbidness and shear cracking were found.

The evaluation criteria A and B are judged as the dental composition possessing a practical stability when it is in the form of paste.

Space-Filling Property to a Metal Mold

A metal mold having a hole with 4 mm φ and 4 mm was filled with each dental composition shown in Table 3 in the form of paste. The dental compositions in the form of paste were evaluated for the space-filling property to a metal mold according to the following evaluation criteria:

A: excellent space-filling property, both the extensibility and the formative property are good;

B: practical space-filling property, either the extensibility or the formative property is good;

C: unpractical space-filling property, either the extensibility or the formative property is inappropriate.

The evaluation criteria A and B are judged as the dental composition possessing a practical space-filling property when it is in the form of paste.

Abrasion Resistance

Each dental composition shown in Table 3 in the form of paste was filled in a columnar clear acrylic mold with a radius of 5 mm and a thickness of 5 mm. The pastes filled in the mold were irradiated at each of top and bottom faces of the pastes at tree times for 3 minutes per one irradiation using SOLIDILIGHT II (Shofu Inc.) to obtain cured products, and the cured products were removed from the mold. One face of the irradiated faces of the cured products was ground to reduce the total length to 4 mm. The surface of the ground face was polished with a rotary polishing apparatus. The cured products having the polished surface were used as test sample. The following abrasion resistance tests were carried out. The difference in the length between the test sample before the abrasion resistance tests and after the tests was a measure of abrasion wear. The lengths were measured at seven positions on each test sample. The averages of the lengths as abrasion wear were summarized in Table 4.

Abrasion Resistance Test 1:

The test samples were put on waterproof abrasive paper #240 so that the polished surface of the test samples contacted with the waterproof abrasive paper in water. A motor shaft was attached to the face opposite to the face having a polished surface of the test samples. A 100 gram weight load was put on the test sample through the motor shaft. The test sample was rotated under the load of weight by driving the motor at one rotation per minute for an hour at 23 degrees Celsius.

Abrasion Resistance Test 2:

Two test samples were set so that the polished surfaces of the samples contacted with each other in water. A motor shaft was attached to the face opposite to the face having a polished surface of the upper test sample. A 100 gram weight load was put on the upper test sample through the motor shaft. The upper test sample was rotated under the load of weight by driving the motor at one rotation per minute for 168 hours at 23 degrees Celsius.

Rate of Polymerization Shrinkage

Each of dental compositions shown in Table 3 in the form of paste was filled in a clear acrylic mold with a thickness of 5 mm, a wide of 1 cm and a length of 5 cm and were irradiated in a similar manner as the abrasion resistance tests to obtain cured products. The seven cured products were removed from the mold. The lengths of the cured products were measured with a micrometer. The rate of polymerization shrinkage for each of products was determined. The averages of the rate of polymerization shrinkage were summarized in Table 4.

TABLE 4

| Sample | Stability | Space-filling property | Abrasion resistance test 1 (mm) | Abrasion resistance test 2 (mm) | Rate of polymerization shrinkage (%) |
|---|---|---|---|---|---|
| Example 1 | B | B | 1.54 | 3.02 | 0.05 or less |
| Example 2 | A | A | 0.87 | 0.53 | 0.05 or less |

TABLE 4-continued

| Sample | Stability | Space-filling property | Abrasion resistance test 1 (mm) | Abrasion resistance test 2 (mm) | Rate of polymerization shrinkage (%) |
|---|---|---|---|---|---|
| Example 3 | A | A | 0.79 | 0.48 | 0.05 or less |
| Example 4 | A | A | 0.76 | 0.55 | 0.20 or less |
| Example 5 | A | A | 0.95 | 0.54 | 0.20 or less |
| Example 6 | A | A | 1.24 | 1.12 | 0.05 or less |
| Example 7 | A | A | 1.42 | 2.08 | 0.05 or less |
| Example 8 | B | A | 1.32 | 1.27 | 0.05 or less |
| Example 9 | B | B | 1.48 | 2.01 | 0.05 or less |
| Example 10 | A | A | 1.19 | 0.77 | 0.05 or less |
| Comparative example 1 | C | C | 1.64 | 2.48 | 0.05 or less |
| Comparative example 2 | C | A | 2.58 | 1.95 | 0.05 or less |
| Comparative example 3 | B | A | 2.46 | 2.04 | 0.05 or less |
| Comparative example 4 | A | A | 3.35 | 2.21 | 1.00 or more |
| Comparative example 5 | A | A | 3.45 | 2.29 | 1.00 or more |

As shown in Table 4, the dental compositions prepared in examples 1 to 10 and comparative examples 3 to 5 had a practical stability and a practical space-filling property when they are in the form of paste. The dental compositions prepared in comparative examples 1 and 2 had an unpractical stability when they are in the form of paste. In addition, the dental composition prepared in comparative example 1 had an unpractical space-filling property when it is in the form of paste.

The abrasion resistance test 1 corresponds to an acceleration test reflecting a situation where hard foods are masticated strongly between the teeth. The abrasion resistance test 2 corresponds to an acceleration test reflecting mastication over the years.

As shown in Table 4, the results of the abrasion resistance test 1 indicated that the cured product of the dental composition prepared in example 1 had a sufficient abrasion resistance as compared with the cured products of those prepared in comparative examples 2 to 5. The results of the abrasion resistance test 1 indicated that the cured products of those prepared in examples 1 to 10 and comparative example 1 had a good abrasion resistance, respectively. The results of the abrasion resistance tests 1 and 2 indicated that the cured products of those prepared in examples 1 to 10 had a sufficient abrasion resistance, respectively. Further, the results of the abrasion resistance tests 1 and 2 indicated that the cured products of those prepared in examples 2 to 5 had a good abrasion resistance, respectively.

As shown in Table 4, the polymerization shrinkage rates of the dental compositions prepared in comparative examples 4 and 5 were 1.00% or more, respectively, and therefore, the dental compositions were unpractical. The dental compositions prepared in examples 1 to 10 and comparative examples 1 to 3 were no more than 0.02% or no more than 0.05%, and thus the dental compositions were practical for producing a dental block, etc.

The cured products of the dental compositions prepared in examples 1 to 10 according to embodiments of the present invention were significantly improved in flexural strength, compressive strength and hardness.

Taken together, these results about the stability and the space-filling property of the dental compositions in the form of paste, and the abrasion resistance tests 1 and 2 for the cured products of the dental compositions and the rates of polymerization shrinkage associated with the polymerization curing indicated that the dental compositions of examples 1 to 10 according to embodiments of the present invention possessed sufficient properties for a dental composition. Further, these results indicated that the dental compositions of examples 2 to 6, 8 and 10 according to embodiments of the present invention possessed good properties as a dental composition. Moreover, these results indicated that the dental compositions of examples 2 to 5 had excellent properties as a dental composition.

Figure 2:
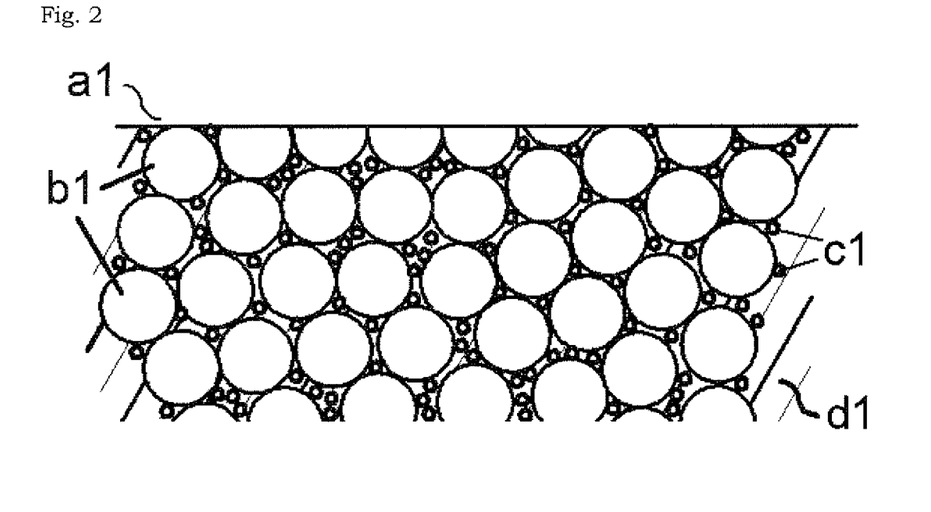
FIG. 2 shows a schematic of a cross-section of a dental composition according to the present invention after curing. The "a1" represents a cross-section of a cured product of which the surface was ground with a CAD/CAM system equipped with a dental router. The "b1" represents a first population of inorganic particles in the cured product. The "c1" represents a second population of inorganic particles in the cured product. The "d1" represents resin matrix of the cured product.
Figure 3:
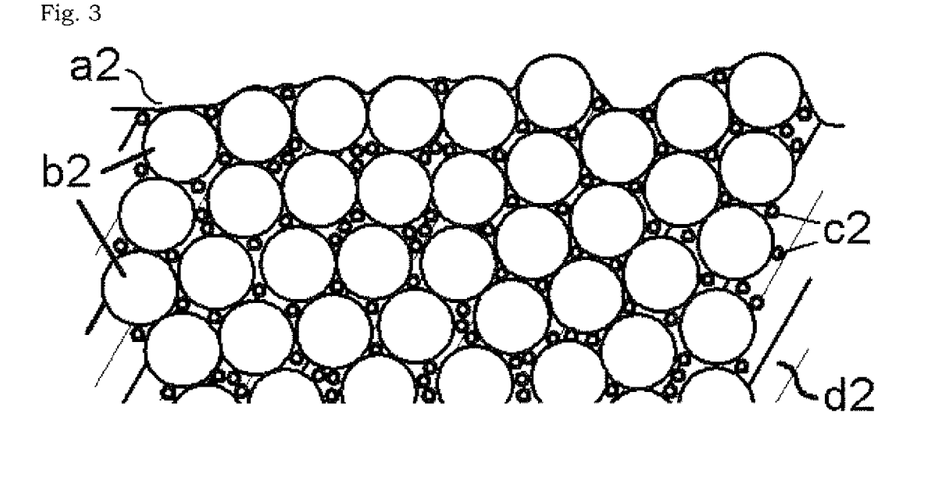
FIG. 3 shows a schematic of a cross-section of a dental composition according to the present invention after curing. The "a2" represents a cross-section of a cured product of which the surface was ground by hand of a dental technician using a dental router. The "b2" represents a first population of inorganic particles in the cured product. The "c2" represents a second population of inorganic particles in the cured product. The "d2" represents resin matrix of the cured product.

The dental composition of example 2 shown in Table 3 when it was in the form of paste was cured by an irradiation using SOLIDILIGHT II (Shofu Inc.) to obtain cured products as a dental block. One of the cured products was ground by a CAD/CAM system equipped with a dental router. The other was ground by hand of dental technician with a dental router. The cured product ground by the CAD/CAM system had a polished uniform surface, as shown in FIG. 2. It was found that the polished surface of the dental block was largely occupied by cross section surfaces of glass particles as filler, resulting in excellent in mechanical strength of the surface. On the other hand, the cured product ground by hand of dental technician had an irregular surface along with the shape of glass particles as filler, resulting in a poor polish.

What is claimed is:

1. A dental composition consisting of a filler, a resin matrix, optionally a coloring pigment, optionally an ultraviolet absorbing agent, optionally a polymerization inhibitor, optionally an anti-discoloring agent, and optionally an anti-microbial agent,
   wherein the filler consists of a first population of particles having an average particle size from 200 to 500 μm, wherein the maximum particle size of the first population of particles is less than 1.4 times the average particle size, and wherein the D30 of particle size distribution of the first population of particles is no less than 0.9 times the average particle size; and
   wherein the amount of the filler is from 85 to 99.5% by weight of the dental composition.

2. The dental composition of claim 1, wherein the first population of particles is inorganic particles.

3. The dental composition of claim 1, wherein the filler is dyed particles.

4. The dental composition of claim 1, wherein the filler is spherical particles.

5. The dental composition of claim 1, wherein the amount of the filler is from 85 to 95% by weight of the dental composition.

6. A dental block or a dental prosthesis, which is formed from the dental composition of claim 1.

7. A dental composition consisting of a filler, a resin matrix, optionally a coloring pigment, optionally an ultraviolet absorbing agent, optionally a polymerization inhibitor, optionally an anti-discoloring agent, and optionally an anti-microbial agent,
   wherein the filler consists of a first population of particles and a second population of particles;
   wherein the first population of particles has an average particle size from 200 to 500 μm, wherein the maximum particle size of the first population of particles is less than 1.4 times the average particle size thereof, and wherein the D30 of particle size distribution of the first population of particles is no less than 0.9 times the average particle size thereof;
   wherein the second population of particles has an average particle size from 20 to 150 μm;
   and wherein the average particle size ratio of the second population of particles to the first population of particles is from 0.1 to 0.3, and the weight amount ratio of the second population of particles to the first population of particles is from 0.05 to 0.5; and wherein the amount of the filler is from 85 to 99.5% by weight of the dental composition.

8. The dental composition of claim 7, wherein the first population of particles is inorganic particles.

9. The dental composition of claim 7, wherein the second population of particles is inorganic particles.

10. The dental composition of claim 7, wherein the first population of particles is inorganic particles and the second population of particles is inorganic particles.

11. The dental composition of claim 7, wherein the filler is dyed particles.

12. The dental composition of claim 7, wherein the filler is spherical particles.

13. The dental composition of claim 7, wherein the amount of the filler is from 85 to 95% by weight of the dental composition.

14. A dental block or a dental prosthesis, which is formed from the dental composition of claim 7.

15. A dental composition consisting of a filler, a resin matrix, optionally a coloring pigment, optionally an ultraviolet absorbing agent, optionally a polymerization inhibitor, optionally an anti-discoloring agent, and optionally an antimicrobial agent, wherein the filler consists of a first population of particles, a second population of particles, and a third population of particles;

wherein the first population of particles has an average particle size from 200 to 500 μm, the maximum particle size of the first population of particles is less than 1.4 times the average particle size thereof, and the D30 of particle size distribution of the first population of particles is no less than 0.9 times the average particle size thereof;

wherein the second population of particles has an average particle size from 20 to 150 μm;

wherein the third population of particles has an average particle size from 1 nm to 1 μm;

wherein the average particle size ratio of the second population of particles to the first population of particles is from 0.1 to 0.3 and the weight amount ratio of the second population of particles to the first population of particles is from 0.05 to 0.5; and wherein the amount of the filler is from 85 to 99.5% by weight of the dental composition.

16. The dental composition of claim 15, wherein at least one of the first population of particles, the second population of particles, and the third population of particles is inorganic particles.

17. The dental composition of claim 15, wherein at least one of the first population of particles, the second population of particles, and the third population of particles is dyed particles.

18. The dental composition of claim 15, wherein at least one of the first population of particles, the second population of particles, and the third population of particles is spherical particles.

19. The dental composition of claim 15, wherein the amount of the filler is from 85 to 95% by weight of the dental composition.

20. A dental block or a dental prosthesis, which is formed from the dental composition of claim 15.

* * * * *